United States Patent [19]

Devidas et al.

[11] Patent Number: 5,051,255
[45] Date of Patent: Sep. 24, 1991

[54] NEMATOCIDAL PREPARATIONS

[75] Inventors: Premachandran Devidas, Grayslake; Aldo J. Crovetti, Lake Forest, both of Ill.

[73] Assignee: Abbott Laboratories, Abbott Park, Ill.

[21] Appl. No.: 258,221

[22] Filed: Oct. 14, 1988

[51] Int. Cl.⁵ .................. A01N 65/00; C12N 1/00
[52] U.S. Cl. .................... 424/195.1; 435/911
[58] Field of Search .............. 424/93, 191.5; 435/911

[56] References Cited

PUBLICATIONS

Chem. Absts. 87:98524t, 1977.
Antagonistic Relationships Between Soil Hyphomycetes and Nematodes (Russian) N. A. Mekhtieva, A. A. Radzhabova, and S. G. Gasanova, Mikologiya i Fitopatologiya 11(5):385–393 (1977) Microbiology Sector, Academy of Sciences of the Azerbaidzhan SSR, Baku.

Primary Examiner—John W. Rollins

[57] ABSTRACT

A new nematocidal agent comprises the fungus, *Myrothecium verrucaria* or metabolites therefrom.

4 Claims, No Drawings

NEMATOCIDAL PREPARATIONS

FIELD OF THE INVENTION

The present invention relates to a new nematocidal agent particularly useful against plant parasitic nematodes and also to a process to prevent damage resulting from nematode infection.

BACKGROUND OF THE INVENTION

Plant parasitic nematodes cause serious economic damage to many agricultural crops around the world. This group of nematodes are microscopic worms and are, in general, obligate parasites of plants. They feed mostly on the roots of host plants; however, several genera are known to parasitize above ground parts including stem, leaves and flowers as well. Almost all the major plant species are susceptible to infection by species of nematodes (notable exceptions are in the marigolds and asparagus). For example, one of the most important genera of plant nematodes, root knot nematodes, (Meloidogyne spp.) is capable of parsitising more than 3,000 species of crop plants. These plants include agronomic crops, vegetables, fruits, flowering trees and shrubs. Nematodes reportedly cause crop loss equivalent to more than U.S. $6 billion in the United States alone and more than U.S. $100 billion around the world.

The symptoms due to phytoparasitic nematode injury varies widely depending on the plant host (even variety), the nematode species (even race), age of the plant, geographical location, climatic conditions etc. In general, an overall patchy appearance of plants in a field is considered indicative of nematode infestation. More specifically, nematode injury results in galling of the roots (abnormal swelling in the tissues due to rapid multiplication of cells in the cortical region) caused by species of root knot (Meloidogyne spp.) and cyst (Heterodera spp.) nematodes, lesions (localized, discolored area) caused by lesion nematodes (Pratylenchus spp.), suppression of cell division resulting in 'stubby' roots (Trichodorus spp.), growth abnormalities including crinkling or twisting of above-ground parts (Aphelenchoides spp.) and even cell necrosis (death) in some cases. Plant parasitic nematodes may be endoparasitic in nature as in the case of the root-knot and lesion nematodes or ectoparasitic as in the dagger nematode (Xiphinema spp.) and lance nematode (Hoplolaimus spp.). Nematodes can be vectors of plant viruses and are also known to induce disease complexes by creating infection courts for the entry of other plant pathogenic fungi and bacteria.

Chemical nematocides as soil fumigants or non-fumigants have been in use for many years and represent one of the few feasible processes for countering nematodes. At present, the process involves repeated applications of synthetic chemicals to the ground prior to planting the crop. These chemicals are extremely toxic to organisms besides nematodes and pose serious threat to the environment. With the renewed emphasis on clean water and air by the United States Environmental Protection Agency, and the detection of many of these active ingredients or the metabolites thereof in ground water and in several non-target organisms, there has been serious concern as to the manufacture and/or use of these chemicals. One of the most effective, economical, and widely used nematocides, DBCP (1,2-dibromo-3-chloropropane) was judged to incite male sterility and possible carcinogenesis an was reported in ground water. Another widely used chemical, EDB (ethylene dibromide), was also found in ground water. Yet another very common insecticide-nematocide, aldicarb (2-methyl-2-(methylthio) propionaldehyde O-(methylcarbmoyl)oxime), was found to be acutely toxic and was found in ground water in several regions of the United States. Carbofuran (2,3-dihydro-2,2-dimethyl-7-benzofuranyl methylcarabmate) and 1,3-D (1,3-dichloropropane), two very commonly used nematocides, are under special review by the EPA, because of their avian toxicity and possible carcinogenic effects.

No known commercially acceptable biological agents have been effective in controlling nematodes to date.

SUMMARY OF THE INVENTION

Myrothecium verrucaria is a cellulolytic fungus of the class Hyphomycetes. A sample of this culture, capable of producing the herein described bio-active metabolite(s), has been deposited, without restriction as to availability, in the permanent culture collection of the American Type Culture Collection at 12301 Parklawn Drive, Rockville, Md. and has been assigned the accession number ATCC 46474.

The mycelial extract and filtrate of this invention, as produced by fermentation of the fungus *M. verrucaria* and the fungus *M. verrucaria* itself exhibit nematocidal activity particularly against *Meloidogyne incognita.* The extract and filtrate of the invention are also active in varying degrees against other nematodes such as *Heterodera glycines*, Hoplolaimus species, Pratylenchus species, Helicotylenchus species, *Aphelenchus avenae,* and Panagrellus species, and the like.

The process for producing a biologically active metabolite under submerged, aerobic, thermophilic conditions comprises cultivating in a nutrient medium *Myrothecium verrucaria,* such as the fungal isolate ATCC No. 46474, wherein an inoculum of the strain is introduced into a fermentor containing a nutrient medium and fermentation occurs, whereupon the fermentation continues until the carbon source of the nutrient medium is substantially consumed. A means of fermentation is by the shake flask method, although various other methods can be used that are well known to those skilled in the art, and do not form the basis of the invention disclosed herein.

A method for control of nematodes comprises administration of an effective amount of a metabolite of the fungus, *Myrothecium verrucaria,* such as the fungal isolate ATCC No. 46474, or the fungus itself to soil infested by said nematodes.

DETAILED DESCRIPTION OF THE INVENTION

The fungus *Myrothecium verrucaria,* such as the fungal isolate ATCC No. 46474, produces a biologically active metabolite or metabolites in various fermentation media. Both the fungus and its metabolites have nematocidal activity and, thus, prevent plant damage from nematodes and control the growth of nematodes. As used herein the phrases "prevent plant damage" and "control of growth" with respect to nematodes means repels, prevents, reduces or eliminates multiplication or reproduction, growth, hatching or the existence of nematodes or nematode eggs.

The term "metabolite" or "extract", as used herein, means the final, isolated, conditioned cell medium obtained by culturing the fungus *M. verrucaria,* such as the fungal isolate ATCC No. 46474, as described herein, i.e., that which is obtained after fermentation of the above fungus. The metabolite can therefore be a solid, as where the fermentation broth is admixed with an organic solvent, including, but not limited to acetone, methanol, petroleum ether, ethyl acetate and the like, to provide a precipitate, or a liquid, as where the post-fermentation broth is used directly or the aforementioned solid is redispersed in an aqueous medium. A preferred organic solvent for the extraction procedure is acetone or methanol. The conditioned cell medium contains one or more bio active components, useful in the control of root-knot and other plant parasitic nematodes.

The methods of using the fungus or metabolites for nematode control are by application of nematocidal compositions comprising the fungus or its metabolites to any field, fruit, vegetable, floral or ornamental crop or nursery crop that is sensitive to attack by plant parasitic nematodes, particularly the Meloidogyne species. Methods of application include direct application to the soil, controlled release of the metabolite in the surrounding soil, application to the plant roots directly before planting in the soil, foliar application and the like.

The term "soil", as used herein is intended to include all media capable of supporting the growth of plants and may include humus, sand, manure, compost and the like.

The process for producing the biologically active metabolite under submerged, aerobic, thermophilic conditions comprises cultivating in a nutrient medium a fungal isolate of *Myrothecium verrucaria,* such as ATCC No. 46474, wherein an inoculum of the isolate is introduced into a fermentor containing a nutrient medium and fermentation occurs, whereupon the fermentation continues until the carbon source of the nutrient medium is substantially consumed. The time for fermentation is preferably, from about 4 days to about 7 days, most preferably about 5 days. The temperature of the fermentation medium is from about 20 to about 40 degrees centigrade. Preferably the temperature is from about 25 to about 30 degrees, and most preferably about 25 degrees centigrade. The pH of the fermentation medium is from about 4 to about 10, preferably from about 5 to about 8, and most preferably at neutral pH. The mycelium and the beer are separated from the fermentation medium by known filtration methods. The mycelium is additionally extracted and then filtered by procedures known in the art, and this filtrate is then repooled with the beer. The remaining solvent is evaporated, the extract frozen and lyophilized to be used as needed.

The term "fermentor", as used herein refers to apparatus used for various types of fermentation methods including, but not limited to, shaken culture, solid-state, continuous and batch fed methods that are contemplated for production of the metabolites of this invention in both laboratory and large scale fermentation processes.

The process of this invention may utilize various media for the initial culture growth and can consist of potato-dextrose agar, Hay infusion agar, corn meal agar, leaf litter agar, PCNB agar, Rose Bengal, Soil infusion (modified), or Yeast Malt Agar as are defined in the Manual of Industrial Microbiology and Biotechnology, Demain and Solomon, American Society for Microbiology, Washington, D.C., 1986.

The metabolites of this invention are produced by the fungus during aerobic fermentation under controlled conditions. The most preferred method for production of the metabolites of *M. verrucaria* is by submerged fermentation.

According to one embodiment of this invention, fermentation is carried out in shake-flasks or in stationary-vat fermentors. In shake-flasks, aeration is provided by agitation of the flask which causes mixing of the medium with air. In the stationary fermentors, agitation is provided by impeller means such as a disc turbine, vaned disc, open turbine, or marine propeller; and aeration is accomplished by injecting air or oxygen into the fermentation mixture.

The fermentation medium consists of suitable sources of carbon, nitrogen, inorganic salts, and growth factors assimilable by the microorganism. Suitable examples of carbon sources are various sugars such as dextrose, glucose, lactose, and maltose, starch, dextrin, corn meal and glycerol.

The sources of nitrogen can be of organic, inorganic or mixed organic-inorganic origin. Examples of nitrogen sources that can be used in the culture medium are soybean meal, corn steep liquor, peanut meal, cottonseed meal, corn germ meal, and various ammonium salts.

The inclusion of certain amounts of minerals and growth factors in the fermentation medium is also helpful. Crude medium ingredients such as distillers' solubles, corn steep liquor, fish meal, yeast products, peptonized milk and whey contain not only minerals but growth factors. However, inorganic salts such as potassium phosphate, sodium chloride, ferric sulfate, calcium carbonate, cobalt chloride, magnesium sulfate, and zinc sulfate can be added to the fermentation medium.

Solid materials, such as calcium carbonate are preferably added in this process, to help with pH control which favors particular types of pellet formation for best results.

The process of producing the metabolites of this invention, while utilizing a shaken culture fermentation technique may also use such a technique for the initial stages of inoculum production as well. Production cultures are started from spores or from specially grown inocula. Growth is generally rapid at first, becoming apparent after 24 hours. It then slows down, giving a concentration of from about 10 to about 30 g of cellular mass per liter after 5 to 7 days, when the stationary phase is usually reached. Growth is then usually thick, consisting of large or small pellets or some kind of sludgy growth with a characteristic appearance and odor. Product formation begins 1 to 3 days after inoculation and continues for 3 to 4 days or more. The production yield depends on the quantity of cells present, their specific activity, and the span of their product-forming capacity.

The inoculum is placed in a liquid medium which is selected empirically for its ability to allow the recovery of the majority of the cells in the population. The spores produced on an initial growth medium, potato-dextrose agar in this case, are transferred into a growth medium contained in a flask (termed seed flask), that would allow for the germination and initial growth of the culture. The germinated spores in an active growth state are then transferred to Erlenmeyer flask (shake-flasks) or stationary-vat fermentors containing the specific fermentation medium. An 1-2% inoculum is typically produced for the fermentation stage of development.

The inoculum medium is within the purview of those skilled in the art, and additional information may be found in the Manual of Industrial Microbiology and Biotechnology, pages 31–40, supra.

A wide range of shaker-culture apparatus may be used in the practice of this invention. The main types of are based on either rotary or reciprocating shaking machines. The process herein preferably uses rotary shakers in which the flasks move in orbits of about 50 mm at about 200 to about 250 rpm, (but may vary between 100 and 500 rpm). The culture moves smoothly around the inside of the flask which is usually an Erlenmeyer flask. The scale-up of the fermentation process is also well known to those skilled in the art and does not form the basis of this invention.

The purpose of shaking in submerged culture is to supply oxygen and nutrients to the growing cells. In shaken cultures, the medium in the fermentation flasks is inoculated with cells or spores, as is the case herein. The strain used as an inoculum is held as a master culture, in the freeze-dried state or at reduced temperatures, e.g. $-70°$ C. The optimal spore concentration to be used for the inoculum is easily determined by those skilled in the art by routine experimentation.

The separation of the metabolite from the fermentation broth and the recovery of these components is carried out by techniques well known in this art. The active components have water solubility and this property may be conveniently employed to recover the metabolite from the fermentation broth.

The following example illustrates the method by which a metabolite is obtained. The described process is capable of wide variation, and any minor departure or extension is considered within the scope of this invention.

EXAMPLE 1

The organism Myrothecium verrucaria, ATCC No. 46474, was grown on a potato-dextrose agar medium consisting of Difco Catalog No. 0013-01-4 media, made up to desired volume with distilled water, and autoclaved at 121.5° C. for 20 minutes. After three to four weeks of growth at 25° C., spores were transferred to a 5 ml vials containing 1 ml of 0.01% Tween-80.

The spore suspension (0.1 ml) was taken from the culture media and inoculated into 100 ml of sterile seed medium [corn steep (10 ml) and glucose (15.6 gm)in 1000 ml of water] in a 500 ml Erlenmeyer flask for culturing with shaking at 28° C. for three (3) days to obtain a seed culture.

From the resulting seed culture, 1–2% was transferred into a fermentation medium [200 ml liters in 500 ml flask; composed of glucose (2 g.), soluble starch (15.0 g), yeast extract (2.0 g), hydrated magnesium sulfate (0.3 g), calcium carbonate (1.0 g), and neopeptone (5.0 g) in 1,000 ml of water at an adjusted pH of 7.0 prior to autoclaving], in shake flasks 25° C. for 5 days with agitation (200 r.p.m.). The fermentation beer after 5 days is colored dark amber; the pH is about 8.1–8.2.

The resulting solution was separated by filtration through two (2) layers of RAPID FLOR® 6½ inch double gauge faced disk (milk) filters.

The mycelium was then steeped in acetone at room temperature for two (2) hours, and then squeezed and filtered to extract the mycelial contents. The residue was then discarded and the filtrate was pooled with the beer. The acetone in this mixture was evaporated and then the extract was frozen and lyophilized. The dry powder, thus prepared, is referred to as the "extract" or "metabolite" and was used as the test material.

The nematocidal activity is found not only in the mycelium extract but also in the filtrate. The morphological and cultural characteristics of *M. verrucaria* are set forth in Compendium of soil fungi, Domsch et al., Volume I, (1980), pages 485–487, and is incorporated herein as reference.

The metabolite is pH stable and produced in generic medium at a pH of about 4 to about 10 initially, resulting in a final pH of about 8. The component is active at a varying temperature range from about 15 degrees to about 35 degrees centigrade. It is also observed that the metabolite develops very rapidly in the fermentation media, as early as 3 days. This would allow for satisfactory production of the active metabolite on full-scale production.

To determine some of the properties and activity of the metabolite, contact assays were utilized. See Balan et al., Production of Nematode-Attracting and Nematocidal Substances by Predacious Fungi, Folia Microbiol, 19, 512–519 (1974).

The contact assay procedure utilized one (1) milliliter (ml) of reconstituted material placed into each well of a 24-well tissue culture plate. The fermentation medium (without fungus), was processed in a similar manner, and sterile water served as a control. Freshly collected second-stage juveniles of root-knot nematodes, *Meloidogyne incognita* were used as the test organism. Approximately 100 nematodes in 50 μl of water were added into each well. The test plate was incubated at 25 degrees C. for a 24 hour period. Nematodes were observed for motility responses after the test period. Four (4) replications were maintained for each treatment and the statistical average of these replications is presented. Unless otherwise indicated (as in Table 2) all temperatures used herein are in degrees centigrade.

A first contact assay was conducted on metabolites after extraction in different solvents, in order to determine suitable extraction solvents. Equal weights of an active and nematocidal preparation from this fungus (prepared as per methods described elsewhere) were mixed well with equal volumes of the different extraction solvents to be tested. The suspension was filtered through Whatman No. 1 filter paper and then through a Millipore filter series (0.80, 0.45 and 0.20 μm). Nematocidal activity in the sterile filtrate was measured by a contact assay using second-stage juveniles of root-knot nematodes and using four times the concentration of metabolite in the growth medium. The metabolite was shown to be water soluble as can be seen from the extraction efficacy in Table 1.

The activity scale for Tables 1 and 2 is as follows:

| | |
|---|---|
| − | no activity |
| + | 50% nematodes dead |
| ++ | 75% nematodes dead |
| +++ | 76–99% nematodes dead |
| ++++ | 100% nematodes dead |

TABLE 1

Nematocidal Activity of Metabolites of *M. verrucaria* After Extraction in Different Solvent

| SOLVENT | | ACTIVITY |
|---|---|---|
| Acetone | 100% | − |
| | 90% | − |
| | 80% | + |

TABLE 1-continued

Nematocidal Activity of Metabolites of *M. verrucaria* After Extraction in Different Solvent

| SOLVENT | | ACTIVITY |
|---|---|---|
| | 70% | + |
| | 60% | + + |
| | 50% | + + + |
| Methanol | 100% | + |
| | 80% | + + + |
| Ethyl acetate | 100% | + |
| | 80% | + |
| Chloroform | 80% | + + |
| Deionized Water | | + + +/+ + + + |
| Lyophilized whole culture | | + + + + |

The activity of the metabolite is substantially unaffected by changes of temperature as seen in Table 2. The extracts were incubated for one hour at various temperatures. Four replications for each of the treatments were performed utilizing the contact assay method.

TABLE 2

Effects of Temperature on Nematocidal Activity

Concentration of extract was 4 times the original broth; e.g. extract prepared from 200 ml of original beer was reconstituted in 50 ml of water to obtain an 4× concentration. Readings were taken 24 hours after incubation at 25° C.

| Temperature °C. | Activity |
|---|---|
| 0 | + + + |
| 25 (room) | + + + |
| 35 | + + + |
| 45 | + + + |
| 55 | + + + |
| 80 | + + + |
| 100 | + + + |
| 121 (autoclave) | + + + |
| water control | − |

The nematocidal activity of the *M. verrucaria* extract was confirmed as demonstrated in Table 3, a see pouch assay; and Table 4 and Table 5 as pot test assays.

The seed pouch assay method as known in the art is generically described in Preiser et al., A Soil-free System for Assaying Nematicidal Activity of Chemicals, Journal of Nematology, Volume 13, Number 4, October 1981, pages 535-537.

As used in this invention, the seed pouch assay is conducted by 1) placing two cucumber seeds (cultivar Straight Eight) into sterilized seed pouches. The pouches are maintained under high humidity conditions and moderate light intensity in a growth chamber. Approximately 5 to 6 days later, when the roots are 4 to 5 inches in length, the pouches are considered to be ready for use in the actual assay procedure; 2) prior to assaying, the dry extract is reconstituted to the desired concentration using sterile water; and 3) 2 milliliters (ml) of the reconstituted extract (at a 4 or 8 times concentration) is pipetted around the root of each seedling. Twenty-four (24) hours later, 2 ml of a suspension of nematodes containing approximately 2000 freshly-collected, infective, second-stage juveniles of root-knot nematodes, *M. incognita* was added to each pouch. Four to six pouches are maintained for each treatment and the remaining pouches are treated with either the fermentation medium or water to serve as controls. The pouches are maintained in the growth chamber and observed for symptoms of nematode infection (root galling) after ten to fourteen (10-14) days. In the case of Table 3 the nematodes were added 24 hours after application of the extracts and the readings were taken 14 days after treatment. The scales used for damage are as illustrated in Table 3.

TABLE 3

Nematocidal Activitvy-Cucumber Seed Pouch

| Treatment | Replicates 1 | 2 | 3 |
|---|---|---|---|
| Control (nematodes added) | +++ | ++++ | ++++ |
| 4× concentration of *M. verrucaria* extract | − | − | − |
| Uninoculated control | − | − | − |

The results are correlated in the following manner for all the Gall Index studies described herein:

| GALL INDEX RATINGS | |
|---|---|
| − | no galls, 100% control |
| + | slight, more than 75% control |
| ++ | moderate, less than 75% control |
| +++ | severe |
| ++++ | total |

The pot test method known in the art is generically described in Di Sanzo et al., Nematode response to Carbofuran, Journal of Nematology, Volume 5, Number 1, January 1973, pages 22-27.

With greenhouse pot tests, four-week old tomato seedlings transplanted into 5" pots in sand are used. The reconstituted material (at 5x, 10x, and 20x concentrations) is pipetted around the root zone of the tomato seedlings. Twenty-four (24) hours later, infective root-knot nematode juveniles (second stage juveniles hatched from eggs—apprx. 5,000/plant) are added to each pot.

After three to four weeks the plants are harvested and the roots observed for symptoms of nematode infection (galling). The commercial nematocide in this instance is aldicarb.

Table 4 is the statistical average of 3 replications of the filtrate and Table 5 is the statistical average of 4 replications from the mycelial extract.

The gall index levels are as described in Table 3. The term "ME" as used hereinbelow means media equivalent or material derived from 1 ml of the growth medium.

TABLE 4

Effect of Filtrate on Nematode Infection

| Treatment | Shoot wt. | Root wt. | Gall Index |
|---|---|---|---|
| No nema. | 88.3 g | 16.5 g | − |
| Nematodes | 87.2 | 19.8 | ++++ |
| Medium | 80.8 | 18.9 | ++++ |
| 100 ME Filtrate | 64.2 | 10.9 | + |
| 33 ME Filtrate | 76.1 | 12.2 | + |

TABLE 5

Effect of Mycelial Extract on Nematode Infection

| Treatment | Shoot wt. | Root wt. | Gall Index |
|---|---|---|---|
| No nema. | 46.3 g | 9.1 g | − |
| Nematodes | 38.5 | 9.2 | ++++ |
| Temik 15G (aldicarb) | 50.0 | 10.9 | − |
| 100 ME Extract | 36.7 | 5.6 | +/− |
| 50 ME Extract | 41.9 | 10.3 | + |

Tables 6 and 7 demonstrate the activity of the metabolite composition in unpasteurized field soil and in sand (Table 6), and in variable types of field soil, autoclaved soil and pasteurized soil (Table 7) as well.

Extracts were applied at the doses mentioned around the root-zone of 4-week old tomato seedlings (CV. Rutgers) grown in 6 inch plastic pots. The plants were maintained in the greenhouse. 24 hours after applications, the plants were inoculated with 5,000 freshly-hatched infective juveniles of root-knot nematodes, *M. incognita*. The plants were harvested 30 days after inoculation. The results are a statistical average of 4 replications.

TABLE 6

Nematocidal Efficacy in Different Soils

| Soil | Dose | Shoot wt (g) | Root wt (g) | Gall Index |
|---|---|---|---|---|
| UnPast. Soil | 1000 ME | 42.2 | 13.1 | +/− |
| | 500 ME | 57.4 | 18.1 | +/− |
| | 250 ME | 70.8 | 19.9 | +/− |
| | NEMA | 81.2 | 26.5 | ++++ |
| | UNTREATED | 79.8 | 22.2 | − |
| SAND | 100 ME | 31.1 | 9.7 | − |
| | NEMA | 65.6 | 28.3 | +++ |
| | UNTREATED | 65.2 | 25.9 | − |

NEMA = refers to untreated, but nematode inoculated soil.

TABLE 7

Effect of Different Soil Types on Nematode Control

| Soil | Dose | Shoot wt (g) | Root wt (g) | Gall Index |
|---|---|---|---|---|
| FIELD | 500 ME | 53.1 | 10.1 | + |
| | 250 ME | 61.9 | 16.3 | + |
| | 0 | 70.3 | 34.0 | ++++ |
| | UNTREATED | 78.7 | 26.7 | − |
| AUTO-CLAVED | 500 ME | 25.6 | 5.9 | − |
| | 250 ME | 27.3 | 5.8 | − |
| | 0 | 58.0 | 30.3 | ++++ |
| | UNTREATED | 62.8 | 19.8 | − |
| PASTEURIZED | 500 ME | 26.4 | 4.7 | + |
| | 250 ME | 41.5 | 7.8 | + |
| | 0 | 58.8 | 29.3 | ++++ |
| | UNTREATED | 67.3 | 20.7 | − |

The metabolite has varying effects upon the eggs of the nematode, *M. incognita*, wherein high or eight-fold concentrations of the metabolite exhibit ovicidal action and low or one-fold concentrations may enhance hatching of the nematode eggs. Data is shown in Table 8 for a contact assay method of testing, as described above, with eggs and not larvae, for the stimulation/inhibition of hatching of the *M. incognita* eggs as a percent increase/decrease over the control. Except for the controls, all the hatched larvae were found to be dead.

TABLE 8

Effect of Metabolite on Stimulation/Inhibition of Egg Hatch

| Hours of Incubation | Water Control (%) | Metabolite Concentration | | |
|---|---|---|---|---|
| | | 1X (%) | 4X (%) | 8X (%) |
| 24 | 100 | 138 | 66 | 13 |
| 48 | 100 | 138 | 75 | 32 |
| 72 | 100 | 230 | 20 | 20 |

$\% = \dfrac{\text{Percent eggs hatched in a treatment}}{\text{Percent eggs hatched in water control}} \times 100$ For the purpose of analysis, the percent of eggs hatched in water control over a 10 day period was considered 100%, while actually, it only ranged from 15–30% in individual replicates. The numbers are an of six replicates.

The fungus and metabolites of this invention can be used to control nematodes for a variety of agricultural applications on many different plants and fruits including, but not limited to, tomatoes, artichokes, aubergines, banana, barley, beetroots, cacao, carrots, cassava, celery, chickpea, citrus, coconut, coffee, corn, cotton, cowpea, eggplant, field bean, forages, grape, guava, melons, millet, oat, okra, ornamentals, papaya, peanut, pepper, pigeon pea, pineapple, potatoes, rice, rye, sorghum, soybean, sugar beet, sugar cane, sweet peppers, sweet potato, tea, tobacco, various lettuces, wheat and yam. Cultivated flowers can be protected according to the present invention, such as carnations, rose bushes, gerberas and chrysanthemums, pot plants, philodendrons, figs, pothos, sansevierias, and cacti; examples of nursery plants would include all the ornamental and flowering shrubs.

The bio-active metabolites can be incorporated into the soil of flower pots or containers, by direct application to the area to be treated at the time of planting, or several days earlier, or by application of the metabolites in a controlled release form. Application can be by granule dispersement on the surface with turnover of the soil by a claw cultivator or a light plow, generally to about 10 cm to 20 cm depth of soil. The effective dose of the active metabolites will depend upon the population of the nematode expected to be encountered, the nematode type, soil, crop, and moisture, etc, and will range from about 10 grams to 100 pounds per acre.

For preparation of agricultural compositions from the metabolites of this invention, inert agriculturally acceptable carriers can be utilized which are either solid or liquid. Solid-form preparations include, but are not limited to, finely dispersible powders, dispersible granules, and the like. Liquid-form preparations such as solutions, emulsions, suspensions, concentrates, emulsifiable concentrates, slurries and the like, may be used depending upon the application intended and the formulation media desired.

The metabolites of this invention may also be formulated as an active composition which may include finely divided dry or liquid diluents, extenders, fillers, conditioners and excipients, including various clays, diatomaceous earth, talc and the like, or water and various organic liquids and mixtures thereof. As the metabolites are water soluble, a drip irrigation method is also possible.

It is also contemplated that the metabolites of this invention may be used in combination with other essential biologicals or beneficial microorganisms or active ingredients, such as herbicides, antimicrobials, fungicides, insecticides, plant growth regulators or nutrients.

Of course, the present invention is not limited to the particular embodiments and modes of operation described herein and it is possible to imagine a certain number of variations in the details without departing from the scope of this invention.

What is claimed is:

1. A nematocidal composition to prevent plant damage by nematodes which comprises one or more metabolites of the fungus, *Myrothecium verrucaria* and a suitable carrier.

2. The nematocidal composition of claim 1 wherein the fungus is isolate ATCC No. 46474.

3. A method for preventing plant damage by nematodes which comprises administration of an effective amount of a metabolite of the fungus *Myrothecium verrucaria* to the locus, soil or seeds of said plants in need of such treatment.

4. The method of claim 3 wherein the fungus is isolate ATCC No. 46474.

* * * * *